United States Patent [19]
Aoyama et al.

[11] Patent Number: 5,817,467
[45] Date of Patent: *Oct. 6, 1998

[54] METHOD FOR QUANTITATIVELY DETERMINING CREATININE KINASE AND A REAGENT THEREFOR

[75] Inventors: Norihito Aoyama; Minako Sakakibara, both of Sunto-gun, Japan

[73] Assignee: Kyowa Medex Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 748,803

[22] Filed: Nov. 14, 1996

[30] Foreign Application Priority Data

Nov. 16, 1995 [JP] Japan .................................. 7-298308

[51] Int. Cl.$^6$ ........................................ C12Q 1/48
[52] U.S. Cl. ............................ 435/15; 435/17; 435/26; 435/188
[58] Field of Search ....................... 435/15, 25, 26, 435/188, 194, 810, 17

[56] References Cited

U.S. PATENT DOCUMENTS

| | | | |
|---|---|---|---|
| 4,286,057 | 8/1981 | Wulff et al. | 435/8 |
| 4,547,461 | 10/1985 | Esders et al. | 435/17 |
| 4,701,420 | 10/1987 | Thunberg et al. | 436/94 |
| 4,740,458 | 4/1988 | Kondo et al. | 435/15 |
| 4,888,289 | 12/1989 | Takami et al. | 435/15 |
| 5,250,420 | 10/1993 | Asano et al. | 435/26 |
| 5,424,204 | 6/1995 | Aoyama et al. | 435/188 |
| 5,496,716 | 3/1996 | Brandt | 435/188 |

FOREIGN PATENT DOCUMENTS

| | | | |
|---|---|---|---|
| 0426100 | 8/1991 | European Pat. Off. | C12N 9/96 |
| 4029585 | 3/1992 | Germany | A61K 9/08 |
| 105199 | 6/1982 | Japan . | |
| 34119 | 5/1984 | Japan . | |
| 248399 | 10/1988 | Japan . | |
| 128799 | 5/1989 | Japan . | |
| 38600 | 6/1993 | Japan . | |
| 59566 | 1/1995 | Japan . | |

OTHER PUBLICATIONS

Clin. Chem., vol. 22, No. 5 (1976) 650–656.

Clin. Chem., vol. 19, No. 2 (1990) 184–188. Japanese.

Scand. J. Clin. Lab. Invest., vol. 36 (1976) 711–723.

Chin et al., Analytical Biochemistry, vol. 214 (1993) 128–134.

*Primary Examiner*—Ralph Gitomer
*Attorney, Agent, or Firm*—Fitzpatrick, Cella, Harper & Scinto

[57] ABSTRACT

The object of the invention is to provide a reagent for quantitatively determining creatine kinase with improved storability in liquid form as well as a method for quantitatively determining creatine kinase with stable measurements. Disclosed are a method for quantitatively determining creatine kinase, which comprises activating creatine kinase in a sample in an aqueous medium in coexistence with a trivalent phosphorus compound and a sulfhydryl-containing compound and then determining creatine kinase activity; a method for stabilizing a sulfhydryl-containing compound, which comprises allowing a trivalent phosphorus compound to coexist with a sulfhydryl-containing compound; and a reagent for quantitatively determining creatine kinase, which comprises a trivalent phosphorus compound, a sulfhydryl-containing compound, and a reaction substrate for creatine kinase.

32 Claims, No Drawings

METHOD FOR QUANTITATIVELY DETERMINING CREATININE KINASE AND A REAGENT THEREFOR

FIELD OF THE INVENTION

The present invention relates to a method for quantitatively determining creatine kinase. The present invention further relates to a method for stabilizing a sulfhydryl-containing compound, as well as a reagent for quantitatively determining creatine kinase which comprises a stabilized sulfhydryl-containing compound.

BACKGROUND OF THE INVENTION

Creatine kinase is present in muscular tissues of the whole body and in the brain, and the measurement of creatine kinase activity is one of the essential items in routine measurement in the field of clinical examination for diagnosis of muscular diseases, neural diseases, brain diseases and cardiac diseases.

Creatine kinase [EC 2.7.3.2] is an enzyme catalyzing the following reaction (I)

where CK is creatine kinase, CP is creatine phosphate, ADP is adenosine diphosphate, C is creatine, and ATP is adenosine triphosphate.

Conventionally, various methods are proposed for quantitative determination of creatine kinase. One of the methods involves quantitatively determining the activity of creatine kinase in the reaction (I) to the left by measuring the formed creatine phosphate or adenosine diphosphate (referred to hereinafter as ADP) in a wide variety of methods.

To measure creatine phosphate, a method of measuring inorganic phosphoric acid resulting from its hydrolysis is known. To measure ADP, there are known methods in which pyruvic acid kinase is allowed to act on ADP in the presence of phosphoenol pyruvic acid, then the resulting pyruvic acid is reacted with 2,4-dinitrophenylhydrazine, followed by measuring the resulting hydrazone; alternatively, lactate dehydrogenase may act on the above pyruvic acid in the presence of reduced nicotinamide adenine dinucleotide (phosphate) [referred to hereinafter as NAD(P)H] to form nicotinamide adenine dinucleotide (phosphate) [referred to hereinafter as NAD(P)] which is then measured.

Another method involves quantitatively determining the activity of creatine kinase in the reaction (I) to the right by measuring the formed creatine or adenosine triphosphate (referred to hereinafter as ATP) in a wide variety of methods.

To measure creatine, a method of measuring it by reacting with e.g. a pigment is known. To measure ATP, the methods known to the art involve using luciferase (Japanese Published Unexamined Patent Application No. 105,199/82), or allowing phosphoglycerate kinase and glyceraldehydephosphate dehydrogenase to act on ATP in the presence of 3-phospho-D-glyceric acid and NAD(P)H and then measuring the resulting NAD(P) (Japanese Examined Patent Publication No. 34,119/84), or allowing hexokinase or glucokinase and glucose-6-phosphate dehydrogenase to act on ATP in the presence of glucose and NAD(P) and then measuring the resulting NAD(P)H [Recommended method for the determination of creatine kinase in human serum, "Rinsho Kagaku" (Clinical Chemistry, 19(2), 184, (1990) (referred to hereinafter as "recommended method")].

Because most creatine kinase in serum is known to be present in inactive form, the enzyme should previously be activated for the accurate quantitative determination of its activity. To activate creatine kinase in inactive form, it is known to preincubate creatine kinase in the presence of an activator in an aqueous medium. Examples of conventional activators are sulhydryl-containing compounds such as N-acetylcysteine, dithiothreitol, reduced glutathione, mercaptoethanol, etc.

However, a reagent composition for quantitative determination of creatine kinase, containing a sulfhydryl-containing compound added as the activator for creatine kinase, has poor stability in an aqueous medium, and a measured activity of creatine kinase using a reagent dissolved in an aqueous medium drops gradually in the storage of the reagent with a prolonged period of time, so it is difficult to realize a reagent dissolved in an aqueous medium for practical measurement method.

This poor storability results mainly from the fact that the sulfhydryl-containing compound particularly N-acetylcysteine added as an activator for creatine kinase is gradually oxidized to form a disulfide compound. This disulfide compound, particularly N-acetylcystine, is known to inhibit creatine kinase activity [Clinical Chemistry, 22(5), 650, (1976)]. To improve the stability of this N-acetylcysteine, it is disclosed that a sulfhydryl-containing compound excluding N-acetylcysteine is allowed to coexist with N-acetylcysteine (Japanese Examined Patent Publication No. 38,600/93), but even if this method is used, it is difficult to maintain the composition stably for a long period of time, mainly because the coexisting sulfhydryl-containing compound itself has poor storability.

Further, the conventional methods for quantitatively determining creatine kinase by activating creatine kinase in a sample with the sulfhydryl-containing compound suffer from the disadvantages that creatine kinase activity is inhibited with even a trace of an oxide formed from the sulfhydryl-containing compound such as N-acetylcysteine, and that some sulfhydryl-containing compounds excluding N-acetylcysteine activate not only creatine kinase but other kinases in the sample to cause an error in quantitative determination. Hence, there is demand for development for a more excellent method for quantitatively determining creatine kinase.

SUMMARY OF THE INVENTION

Recently, a large number of reagents dissolved in an aqueous medium for clinical examination, i.e. not using a lyophilized reagent, are developed and commercially available. The object of the present invention is to provide a method for quantitatively determining creatine kinase with less error in measurements as well as a reagent composition for quantitatively determining creatine kinase with excellent storability.

As a result of their extensive study, the present inventors found that creatine kinase can be quantitatively determined stably by addition of a trivalent phosphorus compound in the method for quantitatively determining creatine kinase activated by a sulfhydryl-containing compound, and that the coexistence of a trivalent phosphorus compound with a reagent for quantitatively determining creatine kinase comprising a sulfhydryl-containing compound leads to stabilization of the sulfhydryl-containing compound and prevents a drop of creatine kinase activity measured by using a stored reagent.

According to the present invention, there are provided a method for quantitatively determining creatine kinase in a sample, which comprises subjecting the creatine kinase in the sample to coexist with a trivalent phosphate compound and a sulfhydryl-containing compound in an aqueous medium to thereby activating the creatine kinase, and then determing the activated creatine kinase activity, a method for stabilizing a sulfhydryl-containing compound by allowing a trivalent phosphorus compound to coexist with the sulfhydryl-containing compound, and a reagent for quantitatively determining creatine kinase, which comprises a trivalent phosphorus compound, a sulfhydryl-containing compound, and a reaction substrate for creatine kinase.

The present invention permits the stabilization of the sulfhydryl-containing compound and provides a reagent for measurement of creatine kinase, which is excellent in storability even in an aqueous medium for a prolonged period of time. Further, there is provided a method for quantitatively determining creatine kinase with improved stability in measurements.

DETAILED DESCRIPTION OF THE INVENTION

According to the present invention, a sulfhydryl-containing compound in an aqueous medium can be stabilized by allowing a trivalent phosphorus compound to coexist with the sulfhydryl-containing compound.

The trivalent phosphorus compound used in the present invention includes, for example, phosphines, diphosphanes, etc.

The phosphines include, for example, substituted or unsubstituted phosphines. The unsubstituted phosphine means $PH_3$ (phosphine). The substituted phosphine may have 1 to 3, same or different substituents which, for example, can be selected from substituted or unsubstituted alkyl, substituted or unsubstituted aryl, substituted or unsubstituted aromatic heterocyclic group, substituted or unsubstituted amino, substituted or unsubstituted carbamoyl, substituted or unsubstituted alkoxy, substituted or unsubstituted acyl, substituted or unsubstituted sulfo, etc. The substituted phosphines substituted with 1, 2, and 3 substituents are referred to primary, secondary, and tertiary phosphines, respectively.

The diphosphanes include substituted or unsubstituted diphosphanes. The unsubstituted diphosphane means $P_2H_4$ (diphosphane). The substituted diphosphane may have 1 to 4, same or different substituents which, for example, can be selected from substituted or unsubstituted alkyl, substituted or unsubstituted aryl, substituted or unsubstituted aromatic heterocyclic group, substituted or unsubstituted amino, substituted or unsubstituted carbamoyl, substituted or unsubstituted alkoxy, substituted or unsubstituted acyl, substituted or unsubstituted sulfo, etc.

The alkyl moiety in the substituted or unsubstituted alkyl may be linear or branched alkyl having 1 to 10 carbon atoms, preferably having 1 to 6 carbon atoms. Examples are methyl, ethyl, propyl, isopropyl, butyl, isobutyl, sec-butyl, tert-butyl, pentyl, neopentyl, hexyl, heptyl, octyl, nonyl, decyl, etc.

The substituted alkyl may have 1 to 3, same or different substituents which, for example, can be selected from aryl, aromatic heterocyclic group, alkoxy, acyl, amino, hydroxy, carboxy, sulfo, phospho, cyano, halogen, etc.

The aryl in the substituted alkyl includes, for example, phenyl, naphthyl, etc. The aromatic heterocyclic group includes, for example, pyridyl, pyrimidyl, naphthilydinyl, furyl, thienyl, pyrazolynyl, imidazolyl, benzofuryl, dibenzofuryl, etc. The alkyl moiety in the alkoxy has the same meaning as described above. The acyl may be linear or branched alkanoyls having 1 to 6 carbon atoms which include, for example, formyl, acetyl, propionyl, butyryl, isobutyryl, valeryl, isovaleryl, pivaloyl, etc., and aroyls which include, for example, benzoyl, naphthoyl, furoyl, thenoyl, nicotinoyl, etc. The halogen represents fluorine, chlorine, bromine or iodine.

The aryl moiety in the substituted or unsubstituted aryl has the same meaning as described above. The substituted aryl may have 1 to 5, same or different substituents which, for example, can be selected from alkyl, alkoxy, acyl, carboxy, alkoxycarbonyl, cyano, amino, sulfo, phospho, halogen, etc. The alkyl, alkoxy, acyl, and halogen have the same meanings as described above, and the alkyl moiety in the alkoxycarbonyl has the same meaning as described above.

The aromatic heterocyclic group moiety in the substituted or unsubstituted aromatic heterocyclic group has the same meaning as described above. The substituted aromatic heterocyclic group may have 1 to 3, same or different substituents which are the same with substituents in the above substituted aryl.

The substituted amino or substituted carbamoyl may have 1 to 2, same or different substituents which, for example, can be selected from substituted or unsubstituted alkyl, substituted or unsubstituted aryl, substituted or unsubstituted aromatic heterocyclic group, acyl, alkoxycarbonyl, etc.

The substituted or unsubstituted alkyl, substituted or unsubstituted aryl, substituted or unsubstituted aromatic heterocyclic group, acyl, alkoxycarbonyl have the same meanings as described above.

The alkoxy moiety in the substituted or unsubstituted alkoxy has the same meaning as described above. The substituted alkoxy may have 1 to 2, same or different substituents which, for example, can be selected from amino, hydroxy, sulfo, phospho, cyano, halogen, etc. The halogen has same meaning described above.

The substituted sulpho may have a substituent which can be selected from substituted or unsubstituted alkyl, substituted or unsubstituted aryl, substituted or unsubstituted aromatic heterocyclic group, etc.

The substituted or unsubstituted alkyl, substituted or unsubstituted aryl, substituted or unsubstituted aromatic heterocyclic group have the same meanings described above.

The primary phosphine includes e.g. methylphosphine, ethylphosphine, propylphosphine, isobutylphosphine, phenylphosphine, 2-napthylphosphine, 2-benzofuranylphosphine, 2-phosphinoethylamine, 4-(phosphinomethyl)imidazole, 1,2,4-butanetriyltris (phosphine), (phenylsulfonyl)phosphine, carbamoylphosphine, etc.

The secondary phosphine includes e.g. dimethylphosphine, diethylphosphine, diisopropylphosphine, diisoamylphosphine, diphenylphosphine, 3,3'-phosphinediyldipropionic acid, 4-(phosphinomethyl)imidazole, 4,4'-phosphinediyldibenzoic acid, etc.

The third phosphine includes e.g. trimethylphosphine, triethylphosphine, tri-n-butylphosphine, tri-n-hexylphosphine, triphenylphosphine, methyldiphenylphosphine, dimethylphenylphosphine, phosphinetriyltridimethylamine, phosphinetriyltridiethylamine, tris(2-methylphenyl)phosphine, tris(3-methylphenyl)phosphine, tris(4-methylphenyl)phosphine, tris(4-methoxyphenyl)phosphine, phosphinetriyltriacetic acid, 3,3',3"-phosphinetriyltripropionic acid, 4,4',4"-phosphinetriyltribenzoic acid, tris(hydroxymethyl)

phosphine, 2,2',2"-phosphinetriyltriethylcyanide, ethyl (phenyl) propylphosphine, acetyldiethylphosphine, etc.

The phosphines cited herein are easily available as commercial products from Tokyo Kasei Kogyo K.K., Pierce Co., Ltd., etc.

The sulfhydryl-containing compound is an activator for creatine kinase and any and every sulfhydryl-containing compound that activates creatine kinase can be used in the present invention. Examples of sulfhydryl-containing compound include, for example, amino acids or peptides such as N-acetylcysteine, cysteine, reduced glutathione, etc.; alcohols such as dithiothreitol, dithioerythritol, mercaptoethanol, thioglycerol, etc.; carboxylic acids such as thioglycolic acid, etc.; saccharides such as thioglucose, etc.; thiouronium salts such as 2-aminoethylisothiouronium bromide, etc. Among the sulthydryl-containing compounds N-acetylcysteine is particularly preferred. Two or more kinds of these sulfhydryl-containing compounds may be used in combination.

The aqueous medium includes e.g. a buffer, a physiological saline-containing liquid, etc., among which a buffer is preferable.

The buffer used may be any one insofar as it does not inhibit creatine kinase activation and creatine kinase activity. Examples are Tris-HCl buffer, imidazole-acetate buffer, phosphate buffer, citrate buffer, malate buffer, oxalate buffer, phthalate buffer, glycine buffer, acetate buffer, succinate buffer, borate buffer, carbonate buffer, Good's buffer, etc.

To stabilize the sulfhydryl-containing compound in an aqueous medium, a trivalent phosphorus compound is added in an amount of preferably 0.005 to 5 mM, preferably 0.01 to 2 mM, relative to 1 mM sulfhydryl-containing compound.

The reagent for quantitatively determining creatine kinase according to the present invention comprises the trivalent phosphorus compound, the sulfhydryl-containing compound and a reaction substrate for creatine kinase, and if necessary the reagent may further contain a reaction substrate for other enzyme, an enzyme, a coenzyme, an activator, a preservative, a stabilizer, a surface active agent, a coloring agent, etc.

The reaction substrate for creatine kinase is selected from the group of creatine phosphate and ADP, or creatine and ATP, depending on the direction of the reaction.

The substrate for other enzyme includes, for example, 3-phospho-D-glyceric acid, glucose, phosphoenolpyruvic acid, luciferin, etc.

The enzyme includes, for example, hexokinase, glucokinase, glucose-6-phosphate dehydrogenase, diaphorase, superoxide dismutase, pyruvate kinase, lactate dehydrogenase, luciferase, etc.

The coenzyme includes, for example, NAD(P), NAD(P)H, etc.

The activator includes, for example, magnesium salts such as magnesium acetate, magnesium sulfate, etc.

The preservative includes, for example, conventional ones such as sodium azide.

The stabilizer includes, for example, metallic chelate agents such as ethylenediaminetetraacetic acid (referred to hereinafter to EDTA), etc. and other general stabilizers e.g. poly saccharides such as soluble starch and derivatives thereof, proteins such as albumin, globulin, etc., water-soluble high-molecular compounds such as polyethylene glycol, etc. Mention may also be made of hydroxylamines and salts thereof, and aldehyde scavengers and salts thereof, reported as stabilizers for glucose-6-phosphate dehydrogenase (Japanese Published Unexamined Patent Application No. 59,566/95), as well as adenosine-5'-phosphate (referred to hereinafter as AMP) and $P^1,P^5$-diadenosine-5'-pentaphosphoric acid (referred to hereinafter as $AP_5A$) to inhibit the effect of other enzymes such as adenylate kinase, etc. in a sample.

The surface active agent includes, for example, Triton X-100, etc.

The coloring agent includes, for example, 2,4-dinitrophenylhyd razine, etc.

The reagent for quantifying creatine kinase according to the present invention can be used in the so-called "one-reagent" system, but it can divided into a "two-reagents" system if necessary for the convenience of an automatic analyzer, etc.

That is, the reagent for quantitatively determining creatine kinase may be in the form of a kit comprising: (1) a reagent comprising a trivalent phosphorus compound and a sulfhydryl-containing compound and (2) a reagent comprising a reaction substrate for creatine kinase. Preferably each reagent in the kit further comprising an aqueous medium.

The aqueous medium includes e.g. a buffer, a physiological saline-containing liquid, etc., among which a buffer is preferable.

The buffer used may be any one insofar as it does not inhibit creatine kinase activation and creatine kinase activity. Examples are Tris-HCl buffer, imidazole-acetate buffer, phosphate buffer, citrate buffer, malate buffer, oxalate buffer, phthalate buffer, glycine buffer, acetate buffer, succinate buffer, borate buffer, carbonate buffer, Good's buffer, etc., and the imidazole-acetate buffer is preferred.

The concentration of the buffer is preferably 1 mM to 2 M, more preferably 10 to 200 mM.

The concentration of the trivalent phosphorus compound is preferably 0.01 to 500 mM, more preferably 0.05 to 250 mM, most preferably 0.1 to 150 mM. The concentration of the sulfhydryl-containing compound is preferably 0.1 to 100 mM, more preferably 0.5 to 50 mM, most preferably 1 to 30 mM.

If the recommended method is adopted for measurement of creatine kinase, the reagent is preferably in the form of a kit comprising: (1) a reagent (referred to hereinafter as first reagent) comprising a buffer, a trivalent phosphorus compound, a sulfhydryl-containing compound, hexokinase or glucokinase, glucose-6-phosphate dehydrogenase, NAD(P), glucose, ADP and optionally an activator, a preservative, a stabilizer, a buffer, etc. and (2) a reagent (referred to hereinafter as second reagent) comprising creatine phosphate, and optionally a stabilizer, etc.

Example of the first reagent is a reagent comprising a trivalent phosphorus compound at preferably 0.01 to 500 mM, more preferably 0.05 to 250 mM, most preferably 0.1 to 150 mM, a sulfhydryl-containing compound at preferably 0.1 to 100 mM, more preferably 0.5 to 50 mM, most preferably 1 to 30 mM, hexokinase (or glucokinase) at preferably 0.1 to 40 U/ml, more preferably 0.2 to 20 U/ml, glucose-6-phosphate dehydrogenase at preferably 0.1 to 40 U/ml, more preferably 0.2 to 20 U/ml, ADP at preferably 0.1 to 20 mM, more preferably 0.2 to 10 mM, NAD(P) at preferably 0.05 to 20 mM, more preferably 0.1 to 10 mM, glucose at preferably 1 to 200 mM, more preferably 2 to 100 mM, magnesium salts at 0.5 to 30 mM, more preferably 2 to 15 mM, AMP at preferably 0.2 to 20 mM, more preferably 0.5 to 15 mM, $AP_5A$ at preferably 1 to 100 $\mu$M, more preferably 2 to 50 $\mu$M, EDTA at preferably 0.1 to 20 mM, more preferably 0.2 to 10 mM, sodium azide at preferably 0.5 to 50 mM, more preferably 1 to 30 mM, and an imidazole-acetate buffer at preferably 1 mM to 2 M, more preferably 10 to 200 mM.

Example of the second reagent is a reagent comprising creatine phosphorate. The concentration of the creatine phosphorate is preferably 15 to 1000 mM, more preferably 30 to 700 mM.

The first reagent is used preferably in an amount of 1 to 20 parts by volume based on 1 part by volume of the second reagent.

The reagent of the present invention can, as a matter of course, contain additives not exemplified, such as an activator, a preservative, a stabilizer, a buffer, an enzyme, a coloring agent, a surface active agent.

Although a part or the whole of the ingredients in the reagent of the present invention may be provided in lyophilized form and dissolved for reconstitution, it is preferably provided as a liquid reagent.

The method for quantitatively determining creatine kinase in a sample according to the present invention is carried out by subjecting the creatine kinase in the sample to coexist with a trivalent phosphorus compound and a sulfhydryl-containing compound in an aqueous medium to thereby activating the creatine kinase; and then determing the activated creatine kinase activity.

As the sample, any sample can be used insofar as it contains creatine kinase. The sample includes e.g. plasma, serum, etc. as well as extracts with extractant from the brain, muscle, heart, etc. The extractant used in extraction includes water, saline, said buffers, etc.

The step of activating creatine kinase in a sample is carried out by adding the sample containing creatine kinase to an aqueous medium comprising the sulfhydryl-containing compound, the trivalent phosphorus compound, and optionally other activator, preservative, stabilizer, etc. and preincubating the resulting aqueous medium at 10 to 50° C. for 1 to 15 minutes, preferably at 25° to 40° C. for 3 to 6 minutes.

After the creatine kinase in the sample is activated by the preincubation, a reagent containing a substrate for creatine kinase is added to the aqueous medium it and the aqueous medium thus formed is incubated at 10° to 50° C. for 1 to 15 minutes, preferably at 25° to 40° C. for 3 to 6 minutes. The activity of the creatine kinase can be determined by measuring the concentration of the product formed from the substrate. Although the concentration of the product can be directly determined in any method known to the art, it is alternatively possible to convert the product in a method known to the art into another compound and determine its concentration in a method known to the art.

To determine creatine kinase, it is preferably to adopt the above-mentioned recommended method which is used most frequently by virtue of its excellent principle, sensitivity, reproducibility, applicability to an automatic analyzer and handling of a large number of samples.

Hereinafter, the recommended method is described in detail.

The principle of this method is shown in the following reaction scheme (II):

(II)

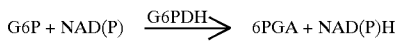

where HK is hexokinase, G6PDH is glucos-6-phosphate dehydrogenase, G is glucose, G6P is glucose-6-phosphate, and 6PGA is 6-phosphogluconic acid.

Creatine kinase in a sample is activated by adding the sample to a reagent comprising a sulfhydryl-containing compound, a trivalent phosphorus compound, hexokinase (or glucokinase), glucose-6-phosphate dehydrogenase, ADP, NAD(P), glucose, imidazole-acetate buffer, and optionally the aforesaid activator, preservative, stabilizer, etc. and then preincubating it at 10° to 50 °C. for 1 to 15 minutes, preferably at 25° to 40° C. for 3 to 6 minutes.

After the creatine kinase in the sample is activated by the preincubation, a reagent comprising creatine phosphate as a substrate for creatine kinase is added to it and the sample is incubated at 10° to 50° C. for 1 to 15 minutes, preferably at 25° to 40° C. for 3 to 6 minutes, and the activity of the creatine kinase is determined by optically measuring the product of NAD(P)H at 340 nm. Alternatively, the NAD(P)H can be measured after reacting with another compound, for example, with a tetrazolium salt, or can be measured by reacting the NAD(P)H with another compound to produce hydrogen peroxide (Japanese Published Unexamined Patent Application No. 248,399/88), or hydrogen peroxide may be formed from the reaction of NAD(P)H catalizing by diaphorase [EC 1. 6. 99.1 or 2] or superoxide dismutase [EC 1. 15. 1. 1] (Japanese Published Unexamined Patent Application No. 128,799/89).

The hexokinase used includes, for example, those derived from yeast, genetically recombined yeast, Bacillus, etc. Glucokinase with higher specificity for glucose than hexokinase can also be used. Any glucokinase can be used irrespective of the source from which it was derived. Further, any glucose-6-phosphate dehydrogenase can be used as well, irrespective of the source from which it was derived.

EXAMPLES

The present invention is specifically described by reference to the following examples which are not intended to limit the scope of the present invention.

Example 1

A reagent solution containing the following ingredients was prepared.

| Reagent I solution: | |
|---|---|
| Imidazole-acetate buffer (pH 6.6) | 115 mM |
| EDTA | 2.3 mM |
| Magnesium acetate | 11.5 mM |
| N-acetylcysteine | 23 mM |
| ADP | 2.3 mM |
| AMP | 5.8 mM |
| AP$_5$A | 11.5 µM |
| Carboxymethoxylamine hydrochloride | 10 mM |
| Glucose | 23 mM |
| NADP | 2.3 mM |
| Hexokinase | 3.45 U/ml |
| Glucose-6-phosphate dehydrogenase | 1.725 U/ml |
| Reagent II solution: | |
| Creatine phosphate | 345 mM |

The phosphorus compound in Table 1 was added at the indicated concentration to Reagent I solution immediately after prepared, and it was stored at 10° C. for 6 months (stored reagent). After 6 months, a reagent with the same composition was prepared (fresh reagent), and both the stored and fresh reagents were used for determination of creatine kinase activity in standard serum according to the method of "Rinsho Kagaku" (Clinical Chemistry), 19(2), 184, (1990), as follows: 50 µl standard serum was added to 2.25 ml Reagent I solution, and the mixture was preincubated at 37° C. for 5 minutes, and then 0.75 ml Reagent II solution was added to it in a reaction cell kept at 37° C. in a spectrophotometer. Two minutes thereafter, the reaction solution was monitored with time over 3 minutes for its absorbance at 340 nm. Creatine kinase activity was estimated in a usual manner using the molecular extinction coefficient of NADPH from the change with time in absorbance. The results are shown in Table 1. The residual reagent activity of the stored reagent is expressed in a relative value, assuming that the reagent activity of the fresh reagent is 100%.

TABLE 1

| Phosphorus Compounds | Concentration (%) | Residual Reagent Activity (%) |
| --- | --- | --- |
| None | | 52.0 |
| Triphenylphosphine | 1 | 87.5 |
| Tris(2-methylphenyl)phosphine | 1 | 91.0 |
| Tris(3-methylphenyl)phosphine | 1 | 90.4 |
| Tris(4-methylphenyl)phosphine | 1 | 88.9 |
| Tris(4-methoxylphenyl)phosphine | 1 | 87.5 |
| 4,4',4"-phosphinetriyltribenzoic acid | 10 | 96.1 |
| Tri-n-butylphosphine | 1 | 84.0 |
| Tri-n-hexylphosphine | 1 | 84.6 |
| Tris(hydroxymethyl)phosphine | 10 | 97.9 |
| 3,3',3"-phosphinetriyltripropionic acid | 10 | 98.0 |
| 2,2',2"-phosphinetriyltriethylcyanide | 10 | 97.3 |
| Phosphinetriyltridimethylamine | 10 | 95.0 |
| Phosphinetriyltridiethylamine | 10 | 94.3 |

Example 2

Reagent Kit A containing the following ingredients was prepared.

| Reagent I solution: | |
| --- | --- |
| Imidazole-acetate buffer (pH 6.6) | 115 mM |
| EDTA | 2.3 mM |
| Magnesium acetate | 11.5 mM |
| N-acetylcysteine | 23 mM |
| ADP | 2.3 mM |
| AMP | 5.8 mM |
| AP$_5$A | 11.5 µM |
| Carboxymethoxylamine hydrochloride | 10 mM |
| Glucose | 23 mM |
| NADP | 2.3 mM |
| Hexokinase | 3.45 U/ml |
| Glucose-6-phosphate dehydrogenase | 1.725 U/ml |
| Dithiothreitol | 10 mM |
| 3,3'3"-phosphinetriyltripropionic acid | 10 mM |
| Reagent II solution: | |
| Creatine phosphate | 345 mM |

Example 3

Reagent Kit A prepared in Example 2 was stored at 10° C. for 6 months. For comparison, a reagent kit (referred to Reagent Kit B) containing the same ingredients as in Reagent Kit A but not containing 3,3',3"-phosphinetriyltripropionic acid was prepared and stored in a similar manner.

After storage, Reagent Kits A and B were used for determination of residual reagent activity in the same manner as in Example 1. The results are shown in Table 2.

TABLE 2

| Reagent Kit | Residual Reagent Activity (%) |
| --- | --- |
| Reagent Kit B | 76.5 |
| Reagent Kit A | 99.6 |

What is claimed is:

1. A method for quantitatively determining creatine kinase in a sample which comprises the steps of:
    contacting the creatine kinase in the sample with a reaction substrate for creatine kinase in the presence of substituted or unsubstituted phosphine and a sulfhydryl-containing compound in an aqueous medium to thereby activate the creatine kinase;
    determining a concentration of a product formed from the reaction substrate; and then
    correlating the concentration of the product with a quantity of the creatine kinase in said sample.

2. The method according to claim 1, wherein the sulfhydryl-containing compound is selected from the group consisting of N-acetylcysteine, cysteine, reduced glutathione, dithiothreitol, dithioerythritol. mercaptoethanol, thioglycerol, thioglycolic acid, thioglucose and 2-aminoethylisothiouronium bromide.

3. The method according to claim 1, wherein the aqueous medium is a buffer.

4. The method according to claim 1, wherein the sulfhydryl-containing compound is selected from the group consisting of amino acids, peptides, alcohols, carboxylic acids, saccharides, and thiouronium salts.

5. A method for stabilizing a sulfhydryl-containing compound, which comprises:
    obtaining an aqueous medium comprising said sulfhydryl-containing compound, and
    admixing substituted or unsubstituted phosphine in said aqueous medium.

6. The method according to claim 5, wherein the sulfhydryl-containing compound is selected from the group consisting of N-acetylcysteine, cysteine, reduced glutathione, dithiothreitol, dithioerythritol, mercaptoethanol, thioglycerol, thioglycolic acid, thioglucose and 2-aminoethylisothiouronium bromide.

7. The method according to claim 5, wherein the aqueous medium is a buffer.

8. The method according to claim 5, wherein the sulfhydryl-containing compound is selected from the group consisting of amino acids, peptides, alcohols, carboxylic acids, saccharides and thiouronium salts.

9. A reagent for quantitatively determining creatine kinase in an aqueous medium, which comprises substituted or unsubstituted phosphine, a sulfhydryl-containing compound, and a reaction substrate for creatine kinase.

10. The reagent according to claim 9, wherein the sulfhydryl-containing compound is selected from the group consisting of N-acetylcysteine, cysteine reduced glutathione, dithiothreitol, dithioerythritol, mercaptoethanol, thioglycerol, thioglycolic acid, thioglucose and 2-aminoethylisothiouronium bromide.

11. The reagent according to claim 9, further comprising a buffer.

12. The reagent according to claim 9, wherein the sulfhydryl-containing compound is selected from the group consisting of amino acids, peptides, alcohols, carboxylic acids, saccharides, and thiouronium salts.

13. A kit for quantitatively determining creatine kinase in an aqueous medium, which comprises:
   i) a first reagent which activates creatine kinase in the presence of substituted or unsubstituted phosphine, and a sulfhydryl-containing compound, and
   ii) a second reagent which determines a concentration of a product formed from contacting activated creatine kinase with creatine phosphate and ADP, or creatine and ATP.

14. The kit according to claim 13, wherein the sulfhydryl-containing compound is selected from the group consisting of N-acetylcysteine, cysteine, reduced glutathione, dithiothreitol, dithioerythritol. mercaptoethanol, thioglycerol, thioglycolic acid, thioplucose and 2-aminoethylisothiouronium bromide.

15. The kit according to claim 13, which further comprises a buffer.

16. The kit according to claim 13, wherein the sulfhydryl-containing compound is selected from the group consisting of amino acids, peptides, alcohols, carboxylic acids, saccharides, and thiouronium salts.

17. A method for activating creatine kinase, which comprises:
   obtaining an aqueous medium comprising said creatine kinase, and
   admixing substituted or unsubstituted phosphine and a sulfhydryl-containing compound in said aqueous medium.

18. The method according-to claim 17, wherein the sulfhydryl-containing compound is selected from the group consisting of amino acids, peptides, alcohols, carboxylic acids, saccharides, and thiouronium salts.

19. The method according to claim 17, wherein the sulfhydryl-containing compound is selected from the group consisting of N-acetylcysteine, cysteine, reduced glutathione, dithiothreitol, dithioerythritol, mercaptoethanol, thioglycerol, thioglycolic acid, thioglucose and 2-aminoethylisothiouronium bromide.

20. The method according to claim 17, wherein the aqueous medium is a buffer.

21. A reagent for activating creatine kinase in an aqueous medium, which comprises substituted or unsubstituted phosphine and a sulfhydryl-containing compound.

22. The reagent according to claim 21, wherein the sulfhydryl-containing compound is selected from the group consisting of amino acids, peptides, alcohols, carboxylic acids, saccharides, and thiouronium salts.

23. The reagent according to claim 21, wherein the sulfhydryl-containing compound is selected from the group consisting of N-acetylcysteine, cysteine, reduced glutathione, dithiothreitol, dithioerythritol, mercaptoethanol, thioglycerol, thioglycolic acid, thioglucose and 2-aminoethylisothiouronium bromide.

24. The reagent according to claim 21, further comprising a buffer.

25. A reagent for stabilizing a sulfhydryl-containing compound in an aqueous medium, which comprises substituted or unsubstituted phosphine.

26. The reagent according to claim 25, wherein the sulfhydryl-containing compound is selected form the group consisting of amino acids, peptides, alcohols, carboxylic acids, saccharides, and thiouronium salts.

27. The reagent according to claim 25, wherein the sulfhydryl-containing compound is selected from the group consisting of N-acetylcysteine, cysteine, reduced glutathione, dithiothreitol, dithioerythritol, mercaptoethanol, thioglycerol, thioglycolic acid, thioglucose and 2-aminoethylisothiouronium bromide.

28. The reagent according to claim 25, further comprising a buffer.

29. A kit for quantitatively determining creatine kinase in an aqueous medium, which comprises:
   i) a first reagent comprising substituted or unsubstituted phosphine, and a sulfhydryl-containing compound,
   ii) a second reagent comprising creatine phosphate and ADP, or creatine and ATP, and
   iii) a third reagent comprising means for determining a concentration of a product formed from contacting creatine kinase with said second reagent.

30. A kit for quantitatively determining creatine kinase in an aqueous medium, which comprises:
   i) a first reagent comprising substituted or unsubstituted phosphine, a sulfhydryl-containing compound, and means for determining a concentration of a product formed from contacting creatine kinase with creatine phosphate and ADP, or creatine and ATP, and
   ii) a second reagent comprising creatine phosphate and ADP, or creatine and ATP.

31. A kit for quantitatively determining creatine kinase in an aqueous medium, which comprises:
   i) a first reagent comprising substituted or unsubstituted phosphine, a sulfhydryl-containing compound, one of creatine phosphate and ADP, or creatine and ATP, and means for determining a concentration of a product formed from contacting creatine kinase with one of creatine phosphate and ADP, or creatine and ATP, and
   ii) a second reagent comprising the the other of creatine phosphate and ADP, or creatine and ATP.

32. A kit for quantitatively determining creatine kinase in an aqueous medium, which comprises:
   i) a first reagent comprising substituted or unsubstituted phosphine, a sulfhydryl-containing compound, and one of creatine phosphate and ADP, or creatine and ATP, and
   ii) a second reagent comprising the other of creatine phosphate and ADP, or creatine and ATP, and means for determining a concentration of a product formed from contacting creatine kinase with one of creatine phosphate and ADP, or creatine and ATP.

* * * * *

UNITED STATES PATENT AND TRADEMARK OFFICE
CERTIFICATE OF CORRECTION

PATENT NO. : 5,817,467

DATED : October 6, 1998

INVENTOR(S): NORIHITO AOYAMA ET AL.

Page 1 of 3

It is certified that error appears in the above-identified patent and that said Letters Patent is hereby corrected as shown below:

TITLE PAGE, ITEM [54]

"CREATININE" should read --CREATINE--;

COLUMN 1

Line 2, "CREATININE" should read --CREATINE--;

COLUMN 3

Line 2, "to" should be deleted;

COLUMN 6

Line 13, "can" should read --can be--;
Line 20, "comprising" should read --comprises--;

COLUMN 7

Line 43, "medium it and" should read --medium and;
Line 53, "preferably" should read --preferable--;

UNITED STATES PATENT AND TRADEMARK OFFICE
CERTIFICATE OF CORRECTION

PATENT NO. : 5,817,467

DATED : October 6, 1998

INVENTOR(S): NORIHITO AOYAMA ET AL.

It is certified that error appears in the above-identified patent and that said Letters Patent is hereby corrected as shown below:

COLUMN 9

Line 1, "prepared," should read --being prepared,--;

COLUMN 10

Line 60, "cysteine" should read --cysteine,--;

COLUMN 11

Line 16, "thioplucose" should read --thioglucose--;
    Line 31, "according-to" should read --according to--;

UNITED STATES PATENT AND TRADEMARK OFFICE
CERTIFICATE OF CORRECTION

PATENT NO. : 5,817,467

DATED : October 6, 1998

INVENTOR(S) : NORIHITO AOYAMA ET AL.

It is certified that error appears in the above-identified patent and that said Letters Patent is hereby corrected as shown below:

COLUMN 12

```
Line 5, "form" should read --from--;
Line 43, "the the" should read --the--.
```

Signed and Sealed this

Twenty-third Day of November, 1999

Attest:

Q. TODD DICKINSON

*Attesting Officer*  *Acting Commissioner of Patents and Trademarks*